United States Patent [19]
Brous

[11] 3,973,572
[45] Aug. 10, 1976

[54] SELF-PURGING APPARATUS FOR DETERMINING THE QUANTITATIVE PRESENCE OF DERIVED IONS

[75] Inventor: Jack Brous, Livingston, N.J.
[73] Assignee: Alpha Metals, Inc., Jersey City, N.J.
[22] Filed: Aug. 12, 1974
[21] Appl. No.: 496,403

[52] U.S. Cl. .............................. 134/57 R; 134/109; 134/113; 210/85; 210/96 R
[51] Int. Cl.² .......................................... B08B 3/04
[58] Field of Search............ 134/13, 57 R, 104, 109, 134/113; 210/85, 96

[56] References Cited
UNITED STATES PATENTS
2,989,965  6/1961  Rod............................... 134/57 R X
3,595,252  7/1971  Conte ................................ 134/109
3,871,914  3/1975  Goffredo et al. ................... 134/109

Primary Examiner—Robert L. Bleutge
Attorney, Agent, or Firm—Lerner, David, Littenberg & Samuel

[57] ABSTRACT

An apparatus for determining the quantitative presence of ions derived from solids, liquids, gases or similar items in which a deionized liquid dissolves the ions from the items, the liquid then is evaluated for conductivity by virtue of the presence of the ions, the liquid is then passed through a deionizer to substantially remove the ions, and again the liquid is re-exposed to the partially cleansed item; the cycle is continued until conductivity indicates that a predetermined degree of deionization has been achieved.

7 Claims, 1 Drawing Figure

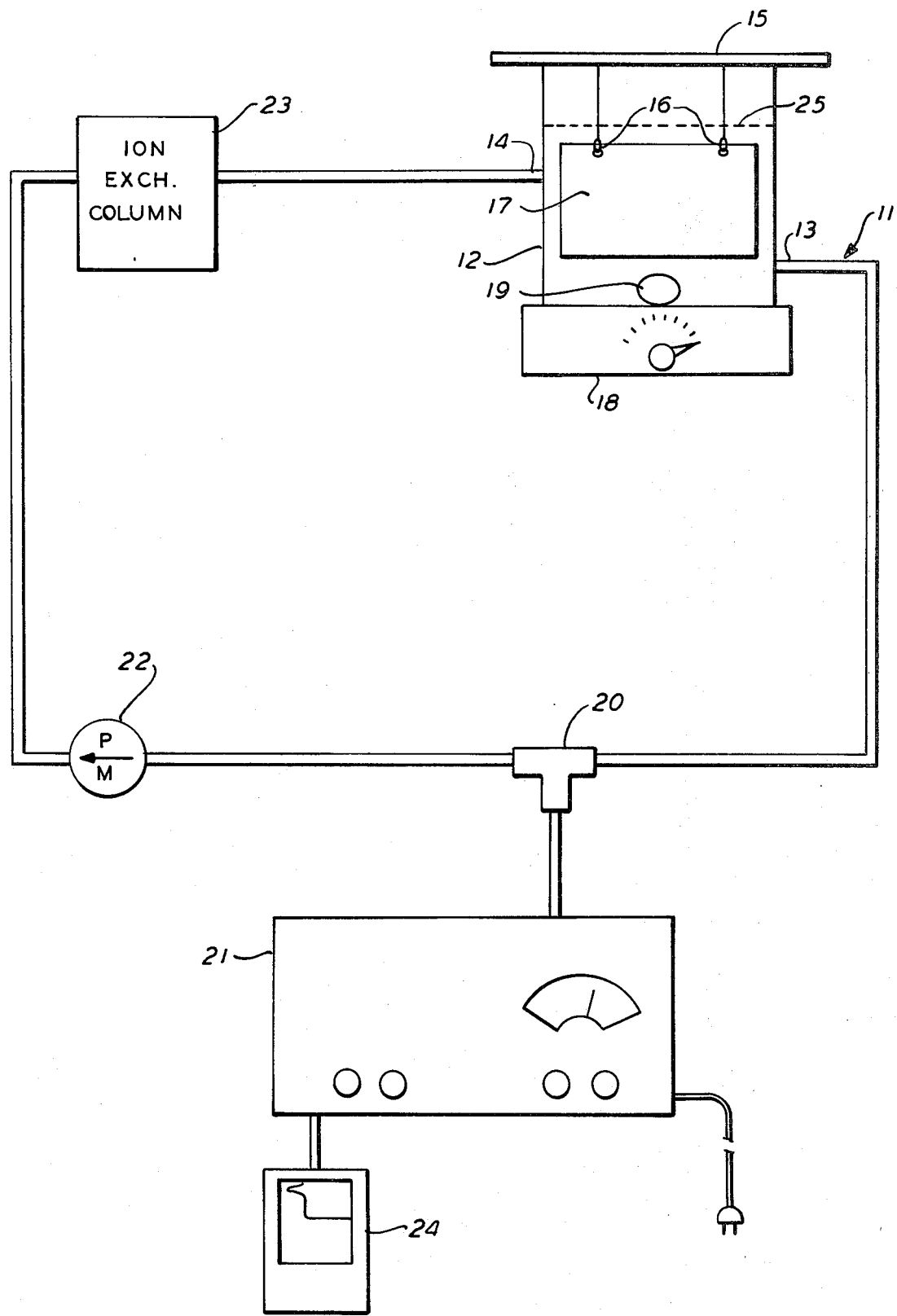

SELF-PURGING APPARATUS FOR DETERMINING THE QUANTITATIVE PRESENCE OF DERIVED IONS

BACKGROUND OF THE INVENTION

1. Field of Invention

This invention relates generally to apparatus and methods for measuring the presence of ionic matter, and particularly to a self-purging deionization apparatus and method for determining the quantitative presence of derived ions from various items where ionic content may be critical.

2. Description of Prior Art

Electronic circuits and electronic components may be impaired by environmental conditions. They are usually shielded from them by some form of protective packaging. However, the presence of ionic contamination residues of processing on the surface of printed circuit boards and components constitutes a danger for which environmental shielding is no protection. Ionic contamination of the surface of printed circuit boards and components may seriously impair reliability and stability. Electrical leakage and corrosion of metallic elements may result. In spite of attempts to provide the highest level of cleanliness, and indeed the purging of electronic circuits and components with suitable solvents, the final circuit assembly may have traces of ionic contamination resulting from prior processing such as plating, etching, handling, fluxing, soldering or the deposition of air-borne contaminants. Bathing electronic circuits and components after fluxing and soldering may not be effective. The use of trichloroethylene, isopropanol, deionized water, or acetone followed by drying may not be completely effective. Certain fluxes are not soluble in water and may erect a protective shield over ionic soils and residues preventing their removal. The essential removal of ionic soils may thus be uncertain.

It is an object of the present invention to provide a very sensitive means for determining the presence of soils on electronic circuits and components. Another object of this invention is to provide a means for quantitatively determining the presence of ionizable material on electronic circuits or components; yet another object of the invention is to provide a means for determining the rate of ionic soil removal from an item; a further object of the invention is to provide a means for determining the ionic contamination of electronic circuits and components, which means will not itself impart contamination to the item being tested. Another object of the invention is to provide a permanent record of the rate and degree of removal of ionic soils from electronic circuits and components.

There are numerous other situations where solids carry ionic material which may even be desirable, but in any event, requires evaluation. The same thing is true of liquids (e.g. preparation of pharmaceutical compounds; ultra pure water for nuclear reactors) and gases (e.g. biology: to measure byproducts of metabolism; ecology: measure levels of sulphur dioxide in the air).

SUMMARY OF INVENTION

These objects and advantages can be achieved by an apparatus in which there is a vessel dimensioned to receive an item to be evaluated. A deionization column is connected to the vessel and a liquid is continuously pumped through the deionization column to the vessel, so that the deionized liquid flows continuously into the vessel. The liquid removes ionizable material from any item in the vessel. The deionization column continuously removes the ions from the liquid, returning the deionized liquid back to the vessel in an uncontaminated state. A conductivity cell is connected between the output of the vessel and the input to the deionizer so that signals will be supplied from the conductivity cell to an appropriate device or monitor to indicate the conductivity of the liquid. The circulation of the liquid throughout the column and the vessel and through the conductivity cell is sustained by a suitable pump.

The liquid circulated through the vessel continuously removes remaining ionizable material which is sensed by the conductivity cell and the material is evaluated by a signal sensing means connected to the cell; the liquid upon passing through the deionizer has the ions removed, and so again circulates through the vessel to remove any remaining ionic material until the reading accomplished by the signal sensing means falls to a particular predetermined level.

THE DRAWINGS

These objects and advantages, as well as other objects and advantages may be attained by the device shown by way of illustration in the drawings in which:

The FIGURE shows a plan view of the apparatus embodying the invention.

PREFERRED EMBODIMENT

The present invention may be embodied in a self-purging apparatus for determining the presence of residual ionic soils and other ionizable materials on electronic circuits and components and provides a recirculation loop 11 wherein there is located a vessel 12 having an outlet 13 and an inlet 14. A bar 15 is provided to rest on the walls of the vessel 12. The bar 15 suspends a pair of clips 16 which hold an electronic circuit or component 17. The vessel 12 may be located on a magnetic stirrer 18. A magnetic spin bar 19 is deposited in the vessel 12. This will accomplish agitation of liquid in the vessel 12. The outlet 13 is connected with the recirculation loop 11 which conducts the effluent liquid to a conductivity cell 20. Conductivity cells are well known items of commerce. A typical cell is available from Balsbaugh Laboratories, Inc., of South Hingham, Mass. The conductivity cell 20 is connected to a continuous reading conductivity meter 21 which registers the conductivity of liquid passing through the conductivity cell 20. Such meters are also well known. The Balsbaugh ICM is typical. The recirculation loop continues from the output side of the conductivity cell 20 to a metering pump 22, which pumps any liquid in the system to an ion exchange column or deionizer 23. Ion exchange columns are well known, and a typical one is Research Model I Ion-Xchanger Cartridge, available from the Illinois Water Treatment Co. of Rockford, Ill. From the deionizer 23, the effluent is conducted to the inlet 14 of the vessel 12.

The conductivity cell 20 is connected to the conductivity meter 21 which may be connected to a recorder 24. Recorders of the type utilized are well known. A typical device is Rustrak Chart Recorders Model 288 (0–2 volts D.C.) available from Recorder Systems Division of Gulton Industries, East Greenwich, R.I. This recorder will mark on a moving chart, the change of conductivity of a liquid leaving the vessel 12 in the loop, and will indicate the time lapse of such record. The test procedure is to operate the pump until the conductivity reading falls to a plateau. The solvent 25 in the system is preferably a mixture of equal parts of isopropanol and water.

A suitable test procedure may be as follows:

With no item in the vessel 12 and the metering pump 22 in continuous operation, a condition is established in which the conductivity reading at the meter 21 is usually 0.1 to 0.05 $\mu$ mhos/cm. (equivalent to 10 to 20 megohms-cm.) An item such as a substrate with residual ionic matter thereon is introduced into the vessel 12. The metering pump 22 circulates the liquid through the loop 11. The conductivity of the liquid sensed by the cell 20 will rise. The conductivity meter 21 will so indicate. The recorder 24 may be used to follow the change of conductivity of the solution with time. The conductivity meter 21 will show a rise to a peak of conductivity, and then will gradually decrease until the conductivity returns to the level originally indicated before the item 17 was introduced. It can then be concluded that no further ionic soils are being removed from the item 17.

The entire amount of ionic material removed from the sample can be related to the integrated conductivity readings over the period of time required to dissolve the material and purge it. At any instant $t$, the number of moles $n_t$ of ionic material within the conductivity cell is $n_t = V_c C_t$ where $C_t$ is the concentration of ions and $V_c$ is the cell volume which is constant. Over an infinite amount of time, the total number of moles of ions passing through the cell, N will be:

$$N = \int_o^\alpha n_t\, dt = V_c \int_o^\alpha C_t\, dt$$

Ordinarily, the concentrations involved in the removal of ionic soils are low ($<10^{-4}$ N), so that relatively complete ionization may be presumed. Therefore:

Conductivity $= L = k\, C$

Then:

$$N = k\, V_c \int_o^\alpha L_t\, dt$$

Therefore the area included under the conductivity/time curve is proportional to the amounts of ionic materials removed from the item.

The meter 21 and the recorder responses are linear with respect to L.

The use of a magnetic stirrer is not essential, but it is found that the stirrer, with several small teflon coated magnetic spin bars deposited in the vessel 12 accomplishes a more uniform distribution of the extracted ions in the vessel 12 and facilitates the ease of measurements of the curves which are obtained upon the recorder 24. When a sodium chloride solution is introduced into the vessel 12, there is a sharp and almost immediate buildup indicated on the chart of the recorder, and the fall-off is likewise quite rapid. On the other hand when an item which is a circuit board which has been fluxed with an activated rosin flux, soldered and cleaned, is introduced into the vessel 12, the recorder 24 will show a much more gradual buildup of conductivity to a peak value. Likewise, there is a much more gradual decline. It is readily apparent that time is a vital factor for the removal of ionic soils.

Pure deionized water has sometimes been found incapable of completely removing water soluble ionic material from items in the vessel 12, particularly where traces of non-water soluble rosin fluxes or oils are present on the substrate after cleaning. The non-soluble materials apparently act to entrap or shield the ionic materials from contact with the water, thereby inhibiting their removal. It has been noted by W. T. Hobson and R. J. Denoon in MATERIAL RESEARCH REPORT NO. 3–72 of the U.S. Naval Avionics Facility at Indianapolis, Ind., that mixtures of water and isopropanol are quite effective in the removal of organic residues such as rosins and also for the removal of water soluble inorganic salts. A preferred mixture is equal volumes of isopropanol and water which has sufficient water to maintain a high level of ionic response in the conductivity measurement, and at the same time is fully capable of dissolving rosin.

By the use of this apparatus and method, freshly generated deionized solvents are continuously utilized and a high level of sensitivity is achieved. In addition, comparisons may be made to determine the quantitative presence of ionic materials extracted from a substrate, in comparison to a test with a known addition amount of sodium chloride; the relative levels of ionic conductivity may be compared and determined. Moreover the rate of ionic extraction is not a controlling factor because the reading of the conductivity meter 21, before the introduction of the item 17 into the vessel 12, will determine when deionization of the item 17 is complete. In addition, the deionizer 23 produces a continuous supply of deionized solvent to the vessel 12, so that there is no concern over contamination from the solutions used, because the effluent from the elements in the apparatus is self-purging. A further desirable result is that the apparatus and method determine what effect the shape, as well as the nature of the material has upon removal of contaminants. Permanent records of these results are graphically depicted in the recorder. Further, the efficacy of various commercial liquid solvents used in process cleaning can be compared.

One of the more important aspects of the invention is the evaluation of the cleansing capacity of solvents. As an example of this purpose, a standard set of circuit boards were prepared. They were epoxy/fiberglass boards of identical dimensions and an etched copper pattern was applied uniformly to each of the boards and each was dipped for one minute in a sequence of solvent rinses at room temperature: Perchlorethylene, Isopropanol, Deionized Water, Acetone (electronic grade). The boards were then air-dried and upon being tested in the apparatus in accordance with the procedures herein set forth, showed a complete absence of ionic material. A standard flux was chosen, and the boards were wave-fluxed, preheated and soldered, each with the same solder and at the same transport rate. Preheaters were set at 450°F. Within a half hour, after soldering, groups of boards were subjected to one of three different cleaning procedures:

1. Cold cleaning with agitation,
2. Vapor cleaning by vapor and distillate only, 3. Vapor cleaning with immersion in a sump, distillate and vapor.

in both instances of vapor cleaning, the liquid in the sump was contaminated by adding 3% by volume of solid activated rosin flux. A small 1-gallon capacity 2-part compartment vapor cleaner was used for the second and third procedure and each one was carried out with a variety of solvents. The board was then tested in accordance with the invented procedure in the apparatus herein, wherein the conductivity meter and the recorder positively evaluated the cleaning effectiveness of various solvent-cleaners and cleaning procedures. The present apparatus demonstrated itself as an effective tool for helping to determine the reliability of electronic components and assemblies by virtue of demonstrating the efficiency of procedures adopted and solvent-cleaners utilized.

Where rosin flux residues remain after cleaning, they will not be dissolved in water used to extract ionic materials. Residual rosin and other non-soluble materials will effectively mask ionic contaminants against pure water solvent. Alcohols and water mixtures are effective to remove organic as well as inorganic contamination, so that entrapped ionic soils are released. This is demonstrated by the use of the present apparatus and method. Other alcohols and polyalcohols may also be used: propanol, ethanol, methanol, butanol, glycerine, ethylene glycol, propylene glycol. Water and alcohols and mixtures thereof are polar solvents, i.e., capable of dissolving ionic material.

In the FIGURE, solid matter is shown being evaluated for ionic content. Gaseous matter may be similarly evaluated by bubbling gas into the vessel 12. Likewise liquid matter may be evaluated by depositing the liquid into the vessel 12.

What is claimed:

1. A self-purging apparatus for measuring the quantitative amount of ions removed from an ion-containing component, said ions being removed from said component by means of a liquid solvent therefor, said apparatus comprising:

a. a liquid-containing vessel having an inlet and outlet, said vessel adapted to contain said ion-containing component, so that any liquid exiting from said vessel passes through said outlet,
   b. a deionizer having an inlet and an outlet,
   c. a conductivity cell having an inlet and an outlet for signaling the presence of ionic matter in said liquid passing through the cell,
   d. conduit means connecting the outlet of the vessel to the inlet of the conductivity cell, so that all of said liquid exiting from said vessel enters said conductivity cell; conduit means connecting the outlet of the conductivity cell to the inlet of the deionizer; and conduit means connecting the outlet of the deionizer to the inlet to the vessel; the conduits, vessel, deionizer and conductivity cell defining a continuous closed loop for circulating said liquid solvent,
   e. means connected in the continuous closed loop to pump said liquid therethrough, said means comprising a metering pump,
   f. means responsive to the signal from the conductivity cell to show the conductivity of the liquid passing through the cell, and
   g. means responsive to the signal from the conductivity cell to provide a signal depicting the degree of conductivity of a liquid passing through the continuous closed loop at the conductivity cell, over a period of time, so that the conductivity over that period of time may be integrated.

2. The apparatus according to claim 1 in which the liquid is a polar solvent.

3. The apparatus according to claim 1 in which the liquid is water.

4. The apparatus according to claim 1 in which the liquid is an alcohol.

5. The apparatus according to claim 1 in which the liquid is a mixture of alcohol and water.

6. The apparatus according to claim 1 and means to agitate the liquid in the vessel.

7. The apparatus according to claim 1 in which the deionizer is an ion exchange column.

* * * * *